United States Patent [19]

Chen et al.

[11] Patent Number: 5,120,413
[45] Date of Patent: Jun. 9, 1992

[54] ANALYSIS OF SAMPLES UTILZING CAPILLARY ELECTROPHORESIS

[75] Inventors: Fu-Tai A. Chen, Brea; James C. Sternberg, Fullerton, both of Calif.

[73] Assignee: Beckman Instruments, Inc., Fullerton, Calif.

[21] Appl. No.: 708,272

[22] Filed: May 31, 1991

[51] Int. Cl.$^5$ .................. G01N 27/26; B01D 57/02
[52] U.S. Cl. .................. 204/180.1; 204/299 R
[58] Field of Search .................. 204/180.1, 299 R

[56] References Cited

PUBLICATIONS

Fujiwara, S. & Honda, S.; "Determination of Cinnamic Acid and Its Analogues by Electrophoresis in a Fused Silica Capillary Tube"; *Anal. Chem.* 58: 1811-1814 (1986).

Otsuka, K. et al; "Quantitation and Reproducibility in Electrokinetic Chromatography with Micellar Solutions"; *J. Chrom.* 396 350-354 (1987).

Chen, Fu-Tai A. et al; "Capillary Electrophoresis-A New Clinical Tool"; *Clin. Chem.* 77/1:14-19 (1991).

Gordan, M. J. et al; "Protocol for Resolving Protein Mixtures in Capillary Zone Electrophoresis"; *Anal. Chem.* 63:69-72.

Jorgenson, J. W. and Lukacs; K. D.; "Capillary Zone Electrophoresis"; *Science* 222:226-272 (1983).

Lauer, H. H. & McManigill, D.; "Capillary Zone Electrophoresis of Proteins in Untreated Fused Silica Tubing"; *Anal. Chem.* 58:166-170 (1986).

Susumu Honda et al "Simultaneous Determination of Reducing Monosaccharides by Capillary Zone Electrophoresis as the Borate Complexes of N-2-Pyridylglycamines" Analytical Biochemistry 176 (1989) 72-77.

Susumu Honda et al "Analysis of the Oligosaccharides in Oval-bumin by High-Performance Capillary Electrophoresis", Analytical Biochemistry 191, (1990), 228-234.

Sabrina Hoffstetter-Kuhn et al "Influence of Borate Compexation on the Electrophoretic Behavior of Carbohydrates in Capillary Electrophoresis" Analytical Chemistry 63 (1991) 1541-1547.

Henk H. Lauer & Douglass McManigill "Capillary Zone Electrophoresis of Proteins in Untreated Fused Silica Tubing" Analytical Chemistry, 58 (1986) 166-170.

Manuel J. Gordon et al "Protocol for Resolving Protein Mixtures in Capillary Electrophoresis" Analytical Chemistry 63 (1991) 69-72.

*Primary Examiner*—John Niebling
*Assistant Examiner*—John S. Starsiak, Jr.
*Attorney, Agent, or Firm*—William H. May; P. R. Harder; Richard P. Burgoon, Jr.

[57] ABSTRACT

Method and electrolyte buffer useful in the analysis of samples comprising glycoproteins by capillary zone electrophoresis. The buffer comprises at least one agent capable of complexing with sugar moieties of glycoproteins. The buffer preferably further comprises at least one pH modifier. An embodiment of the buffer comprises boric acid as the complexing agent and sodium hydroxide as the pH modifier.

11 Claims, 7 Drawing Sheets

ANALYSIS OF SAMPLES UTILZING CAPILLARY ELECTROPHORESIS

RELATED APPLICATION

The present application is related to U.S. application Ser. No. 07/708,144, entitled "QUANTITATION OF SAMPLES UTILIZING CAPILLARY ELECTROPHORESIS" and U.S. application Ser. No. 07/708,272, entitled "IDENTIFICATION OF SAMPLE CONSTITUENTS UTILIZING CAPILLARY ELECTROPHORESIS, both filed simultaneously herewith by Fu-Tai A. Chen.

FIELD OF THE INVENTION

The present invention is related to analysis of samples in general, analysis by capillary zone electrophoresis in particular, and specifically to electrolyte buffers useful in open capillary zone electrophoresis.

BACKGROUND OF THE INVENTION

The articles set forth in the Background of the Invention are each incorporated herein by reference.

Mammalian proteins, for example, those derived from clinical samples such as whole blood, serum, plasma, cerebrospinal fluid, and urine, are useful as indicators of a disease state or a bodily condition. The amount and type of these proteins in the sample can provide a wealth of information to the investigator.

For example, the protein components of serum include albumin, alpha-1 lipoprotein, alpha-2 macroglobulin, beta-1 lipoprotein and immunoglobuiins (including gammaglobulins). Albumin, the major protein of serum, is usually present in a concentration of between 4.0 and 5.0 g/dL. Decreased concentration of albumin can be indicative of renal disease; increased concentration of albumin is characteristic of dehydration. Elevations of alpha-1 lipoprotein can be indicative of chronic alcoholism or hyperestrogenism due to, e.g., pregnancy. Elevated levels of beta-1 lipoprotein can be indicative of increased cholesterol levels.

Mammalian proteins are charged proteins containing both cationic and anionic moieties. They thus lend themselves to analysis by capillary zone electrophoresis ("CZE"). CZE is a technique which permits rapid and efficient separations of charged substances. In general, CZE involves introduction of a sample into a capillary tube, i.e. a tube having an internal diameter of from about 10 to about 2000 microns and the application of an electric field to the tube. The electric potential of the field both pulls the sample through the tube and separates it into its constituent parts. i.e., each of the sample constituents has its own individual electrophoretic mobility; those having greater mobility travel through the capillary tube faster than those with slower mobility. As a result, the constituents of the sample are resolved into discrete zones in the capillary tube during their migration through the tube. An on-line detector can be used to continuously monitor the separation and provide data as to the various constituents based upon the discrete zones.

CZE can be generally separated into two categories based upon the contents of the capillary columns. In "gel" CZE, the capillary tube is filled with a suitable gel e.g., polyacrylamide gel. Separation of the constituents in the sample is predicated in part by the size and charge of the constituents travelling through the gel matrix. In "open" CZE, the capillary tube is filled with an electrically conductive buffer solution. Upon ionization of the capillary, the negatively charged capillary wall will attract a layer of positive ions from the buffer. As these ions flow towards the cathode, under the influence of the electrical potential, the bulk solution (i.e., the buffer solution and the sample being analyzed), must also flow in this direction to maintain electroneutrality. This electroendosmatic flow provides a fixed velocity component which drives both neutral species and ionic species, regardless of charge, towards the cathode. The buffer in open CZE is as stable against conduction and diffusion as the gels utilized in gel CZE. Accordingly, separations can be obtained in open CZE quite similar to those obtained in gel-based electrophoresis.

Fused silica is principally utilized as the material for the capillary tube because it can withstand the relatively high voltage used in CZE, and because the inner walls ionize to create the negative charge which causes the desired electroosmatic flow. The ionization of the inner walls of the capillary tube does, however, create problems with respect to separation of proteins.

This is because proteins are hetero-polyelectrolytes (i.e. an approximate equivalent number of positively and negatively charged moieties within the molecule when the molecule itself has a neutral-charge). Thus, when ionized, a protein species can have a net positive charge distribution such that the protein species will adsorb quite strongly onto the inner wall. This adsorption leads to artificial zone broadening in CZE, thus leading to inconclusive, erroneous or incomprehensible results.

One proposed attempt at solving this problem was to treat, or "coat", the inner wall of the capillary tube so that electroosmotic flow would be reduced when voltage was applied. That would, in turn, reduce adsorption of proteins onto the tube. Glycol modified fused silica capillaries have been used for serum protein analysis, but only with limited success. See Jorgenson, J. W. & Lukacs, K. D. "Capillary Zone Electrophoresis." *Science* 222:266–272 (1983). This is because treated fused silica capillaries have a relatively short shelf-life and their coatings have a tendency to "dissolve" in an unpredictable manner. The aura of unpredictability is unacceptable in any environment where multiple samples will be analyzed on a frequent basis.

Another proposed solution to this problem was to use a buffer having a pH greater than the isoelectric points (pI) of the protein components of the sample. As is well known, when the pH is equal to the pI, the positive and negative moieties of the molecule are balanced. Similarly, when the pH is greater than pI, the negative moieties predominate and when the pH is less than the pI, the positive moieties exceed the negative moieties. For example, the pI of albumin is 4.6; therefore, at pH 4.6, the negatively charged and positively charged moieties of albumin are equal and the overall charge is neutral. However, as the pH is raised above the isoelectric point, the negatively charged moieties predominate and the net charge is negative. Thus, under the influence of a high pH buffer, all of the protein species of the sample will have a negative charge and will be repelled from the negatively charged wall. This will, in turn, avoid or at least greatly diminish their surface adsorption. However, large pH-pI differences can cause structural changes in the protein or even hydrolysis. Attempts to electrophorese proteins in untreated fused-silica capillary tubes using buffer solutions having pH ranges from 8-11 have resulted in irreproducible migration of all sample zones. See Lauer, H. H. and McManigill, D. "Capillary Zone Electrophoresis of Proteins in Untreated Fused Silica Tubing." *Anal. Chem.* 58:166-169 (1986).

It has been theorized that protein adsorption onto the untreated fused capillary wall is due to ion exchange interactions between cationic sites in the protein and silicate moieties in the wall. See Jorgenson, J. W. "Capillary Electrophoresis", Chpt. 13, *New Direction in Electrophoretic Methods.* ACS Symp. Ser. 335, 1987 (Jorgenson, J. W. & Phillips, M., Eds.). Accordingly, it has been suggested to use high salt buffer conditions to reduce protein adsorption. See Lauer, H. H. & McManigill, D., *Trends Anal. Chem.* 5:11 (1986). However, increasing the salt concentration of the buffer has the effect of increasing the conductivity of the capillary tube which can dramatically increase the heat inside the tube. Increasing temperature causes the migrating zones to become diffused, thus decreasing resolution of the zones. In order to avoid such heat build-up, the electric potential applied to the capillary tube must be greatly diminished. This, however, has the undesirable effect of increasing the time necessary for analysis of the sample.

Because capillary zone electrophoresis is such an extremely powerful tool for the separation of ionic species, a need exists for CZE analysis of protein and protein-portion ("peptide") samples which does not suffer from the severe and deleterious drawbacks noted above.

SUMMARY OF THE INVENTION

The present invention satisfies these needs, by providing a buffer useful in the analysis of clinical samples in CZE utilizing untreated capillary tubes.

The buffer comprises at least one agent capable of complexing with sugar moieties of glycoproteins. Examples of the complexing agent include boric acid, borate-based derivatives, such as, for example, alkylboronic acid having from about 1 to about 20 carbon atoms in the alkyl portion, the alkali-metal salts of phosphate ($PO_4$), mono-, di-, tri-, and tetra-alkyl ammonium phosphate having from about 1 to about 8 carbon atoms in the alkyl portion, the alkali-metal salts of carbonate ($CO_3$), and mono-, di-, tri, and tetra-alkyl ammonium carbonate having from about 1 to about 8 carbon atoms in the alkyl portion.

A pH modifier is preferably added to the buffer. By "pH modifier" is meant an agent that is useful in adjusting the pH of the buffer, which is compatible with the complexing agent, and which preferably includes a monovalent cation. Suitable pH modifiers include alkali-metal hydroxides, such as lithium hydroxide, sodium hydroxide, potassium hydroxide, rubidium hydroxide, cesium hydroxide, francium hydroxide, and mono-, di-, tri-, and tetra-alkyl ammonium hydroxide having from between about 1 and about 8 carbon atoms in the alkyl portion.

The pH of the buffer is greater than the pI of substantially all of the constituents of the sample being analyzed. The pH modifier can be added to the buffer comprising at least one complexing agent such that the pH of the buffer is greater than a designated pI.

DETAILED DESCRIPTION OF PREFERRED EMBODIMENTS

Figure 1:
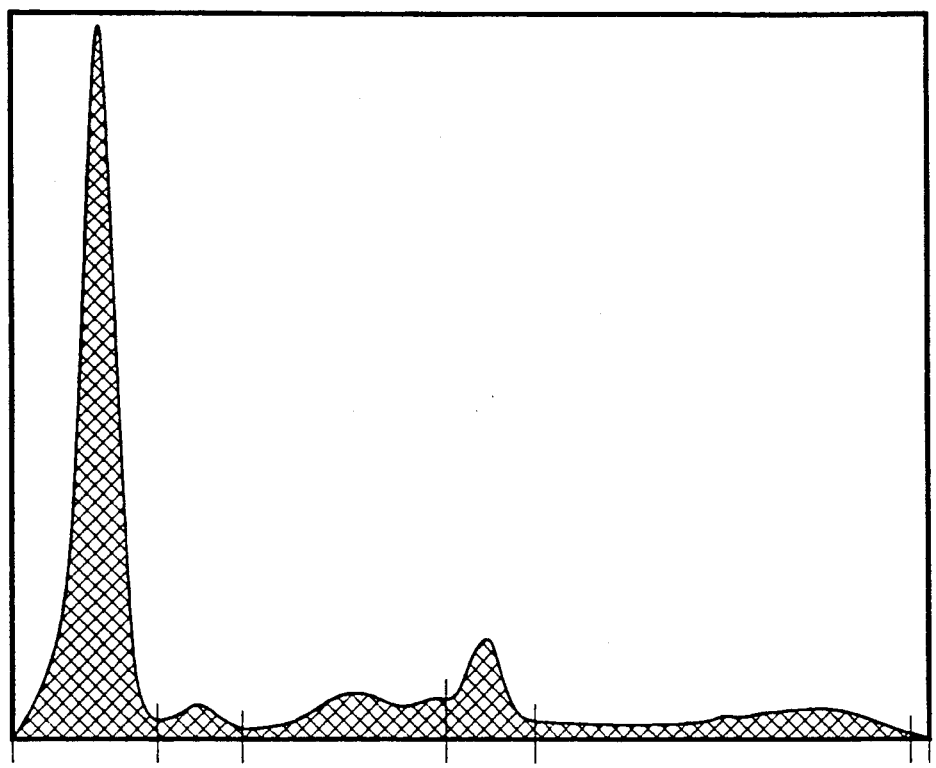
FIG. 1 is an electropherogram of a normal control serum sample separated into its constituents by slab electrophoresis.

Mammalian secreted proteins, unlike non-mammalian secreted proteins (for example, those produced by recombinant DNA technology utilizing *E. coli* as the bacteria) are primarily glycoproteins, that is, they include sugar moieties on their back-bone. Schematically, such proteins can be represented as follows:

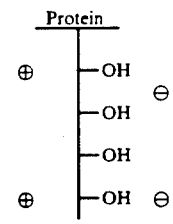

The symbols are indicative of the individual charges that are included within the protein. This charge distribution, referred to as hetero-polyelectrolytic, indicates that when the isoelectric point (pI) equals the pH, the charge distribution of positively and negatively charged moieties will be equal and the net protein charge neutral. When pH is greater than pI, the charge distribution of the protein provides a net negative charge.

CZE techniques have been successfully applied to the analysis of non-mammalian secreted proteins utilizing untreated capillaries. It is only with mammalian proteins that the foregoing problems have been encountered. Applicants believe that because non-mammalian secreted proteins are not glycoproteins, the sugar moieties of mammalian proteins may play a role in the adsorption problem.

Applicants avoid the above problems by including in the electrolytic buffer at least one agent capable of complexing with the sugar moieties of mammalian proteins. The agent, in effect, functions as a protecting group which binds to the protein to prevent its adsorption to the capillary wall while at the same time not affecting the protein itself.

Examples of the agent include boric acid, borate-based derivatives, such as, for example, alkylboronic acid having from about 1 to about 20 carbon atoms, more preferably from about 1 to about 8 carbon atoms and most preferably about 1 carbon atom, the alkali-metal salts of phosphate ($PO_4$) (lithium phosphate, sodium phosphate, potassium phosphate, rubidium phosphate, cessium phosphate, francium phosphate), mono-, di-, tri-, and tetra-alkyl ammonium phosphate having from about 1 to about 8 carbon atoms in the alkyl portion, preferably from about 1 to about 3 carbon atoms, and most preferably 1 carbon atom, the alkali-metal salts of carbonate ($CO_3$) (lithium carbonate, sodium carbonate, potassium carbonate, rubidium carbonate, cessium carbonate, and francium carbonate), and mono-, di-, tri, and tetra-alkyl ammonium carbonate having from about 1 to about 8 carbon atoms in the alkyl portion, preferably from about 1 to about 3 carbon atoms, and most preferably 1 carbon atom. In the most preferred embodiment of the invention, boric acid is the complexing agent.

The concentration of the agent in the buffer is selected so that the agent is present in excess of the amount necessary to bind with the protein constituents in the clinical sample. This ensures that all of the sugar moieties of the protein constituents will be complexed by the agent. Accordingly, the concentration of the agent in the buffer should be in stoichiometric excess relative to the the concentration of the proteins in the sample. Preferably, the concentration of the agent in the buffer is greater than about 20 mM. Boric acid and borate based derivatives are preferably present in concentrations of between about 70 mM and about 400 mM and more preferably between about 75 mM and about 250 mM. The most preferred concentration for boric acid is about 80 mM. With respect to the derivatives of both phosphate and carbonate, these should be present in concentrations of from about 20 mM to about 100 mM.

The pH of the buffer is greater than the pI values for substantially all of the constituent species in the sample being analyzed. This ensures that substantially all of the constituent species have the required net negative charge. For clinical samples, this requires a pH greater than about 8.00, preferably between about 9.00 and about 12.00, more preferably between about 10.00 and 11.00. In the most preferred embodiment, the pH is about 10.25±0.10. These pH values are above the isoelectric points of substantially all protein species of clinical samples.

Boric acid complexes with sugar moieties of glycoproteins at pH above about 8.0, and boric acid has a good buffering capacity between pH of about 8.0 to about 10.0. Thus, at above pH of about 8.0, boric acid interacts with the sugar moieties of glycoproteins, represented schematically as follows:

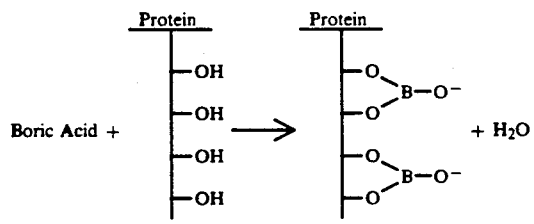

Under such conditions, the protein-borate complex maintains a net negative charge, and the boric acid does not otherwise affect the protein.

Upon ionization, the inner wall of an untreated capillary will be negatively charged. The protein-borate complex, which is also negatively charged, will have a tendency to be repelled by the negatively charged inner-wall. Therefore, adsorption of the complex to the negatively charged inner wall of the capillary is prevented or greatly reduced.

A pH modifier is preferably added to the buffer to maintain the pH of the buffer above the isoelectric points of the constituent species of the sample being analyzed. The pH modifier preferably includes a monovalent cation because polyvalent cations will have a tendency to bind to the negatively charged inner wall of the untreated capillary such that the electroosmotic flow through the capillary will be compromised. Examples of the pH modifier include the alkali-metal hydroxides (lithium hydroxide, sodium hydroxide, potassium hydroxide, rubidium hydroxide, cessium hydroxide and francium hydroxide), mono-, di-, tri-, and tetra-alkyl ammonium hydroxide having from between about 1 and about 8 carbon atoms in the alkyl portion, preferably between 1 and 3 carbon atoms and most preferably 1 carbon atom. In the most preferred embodiment of the invention, the pH modifier is sodium hydroxide.

The amount of pH modifier added to the buffer should be effective to adjust and maintain the pH of the buffer comprising the agent above the isoelectric point of the constituent species in the sample. Accordingly, by determining the pH of the buffer comprising the agent, the investigator can readily determine the amount of pH modifier to be added to the buffer by, for example, monitoring the pH of the buffer as the pH modifier is being added.

A most preferred electrolyte buffer in accordance with the present invention can be prepared as follows:

| | |
|---|---|
| Boric acid (MW 61.83) | 4.95 g |
| Sodium Hydroxide (MW 40.00) | 4.86 g |
| Distilled Water | 1L |
| pH (adjusted by dropwise addition of 1N NaOH) | 10.25 ± 0.10 |

Sodium hydroxide can be added in the indicated amount directly to the buffer in order to increase the pH of the buffer comprising the boric acid. i.e, in the absence of sodium hydroxide, the pH of the boric acid solution is about 8.00, and the addition of the sodium hydroxide results in a pH of about 10.00. The final pH can then be adjusted by the dropwise addition of sodium hydroxide until the final pH is about 10.25.

EXAMPLES

The following examples directed to preferred embodiments of the invention disclosed herein are not intended, nor should they be construed, as limiting the disclosure, or the claims to follow.

I. MATERIALS AND METHODS

A. Capillary Electrophoresis Procedures

Capillary electrophoresis of clinical samples was performed on a Beckman Instruments, Inc. high performance capillary electrophoresis system (Beckman Instruments, Inc., Fullerton, Calif., USA, Model No. 357575) Data analysis was performed on System Gold ™ software (Beckman Instruments, Inc.). The aforementioned capillary electrophoresis system contains builtin 214, 254, 280 and 415 nm narrow-band filters for online detection. Electrophoresis was performed in a fused-silica tube, 75 μm i.d. and 25 cm long (Polymicro Technologies, Inc., Phoenix, Ariz., USA, Part No. TSP075375). The detection window is located approximately 6.5 cm from the column outlet.

Clinical samples were placed on the inlet tray of the above-described capillary electrophoresis system. Clinical samples were automatically injected into the capillary tube by the electrokinetic method for 3 to 10 seconds at 1 kV. Clinical sample separations were performed in less than 10 minutes using a column voltage gradient of 200 volts/cm. The capillary tube was washed and reconditioned between each run (18 seconds, 1N NaOH, 12 seconds, 0.1% Triton-X 100 ™ in distilled $H_2O$).

B. Agarose Gel Electrophoresis

Comparative serum protein analysis and hemoglobin assay analysis by agarose gel electrophoresis ("slab" electrophoresis) was performed on a PARAGON® electrophoresis system using SPE gel (Beckman Instruments, Part No. 655905; PARAGON® is a registered trademark of Beckman Instruments, Inc.). All procedures were performed according to manufacturer's instructions.

C. Control and Patient Samples

Control samples of serum protein were obtained from Beckman Instruments, Inc., Fullerton, Calif. Normal serum and urine samples (Beckman Instruments, Inc., Brea, Calif.) were utilized. Patient serum, urine and cerebro spinal fluid samples were obtained from Brea Community Hospital, Brea Calif.

Serum samples were diluted 1:20 serum to buffer; the buffer contained 75 mmol/L sodium chloride and 20 mmol/L potassium phosphate; the pH of the buffer was 7.0. Urine and cerebro spinal fluid samples were used as received.

D. Electrolyte Buffer

All chemicals were at least of ACS grade. Electrolyte buffer was made by dissolving 4.95 g of boric acid (MW 61.83) and 4.86 g sodium hydroxide (MW 40.00) in 1 L distilled $H_2O$. Final concentration of boric acid was 80 mM/L and sodium hydroxide was 121.6 mM/L. Final pH was adjusted to 10.25±0.1 by dropwise addition of 1N NaOH.

Capillary washing and reconditioning solutions were as described above.

II. EXAMPLES

Example 1

Normal Control Serum Slab Electrophoresis

The aforementioned normal control serum was analyzed by SPE gel on the aforementioned PARAGON®gel electrophoresis system and produced the electropherogram in FIG. 1.

Example 2

Normal Control Serum CZE

Figure 2:
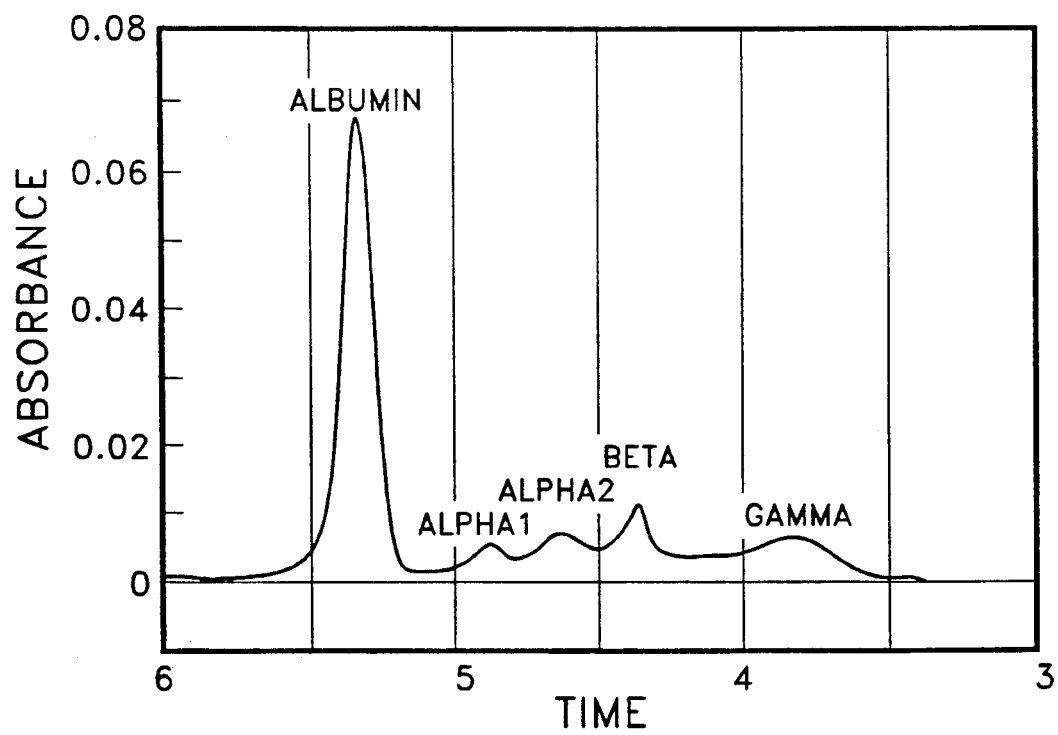
FIG. 2 is an electropherogram of the normal control serum sample of FIG. 1 separated into its constituents by CZE.

The control utilized in Example 1 was analyzed using the aforementioned Beckman capillary zone electrophoresis systems, with detection at 214 nm and an applied potential of 5kV. Analytical results were obtained in less than 10 minutes. The analysis produced the electropherogram in FIG. 2.

Example 3

Serum Sample—IgG Kappa Myeloma Slab Electrophoresis

Figure 3:
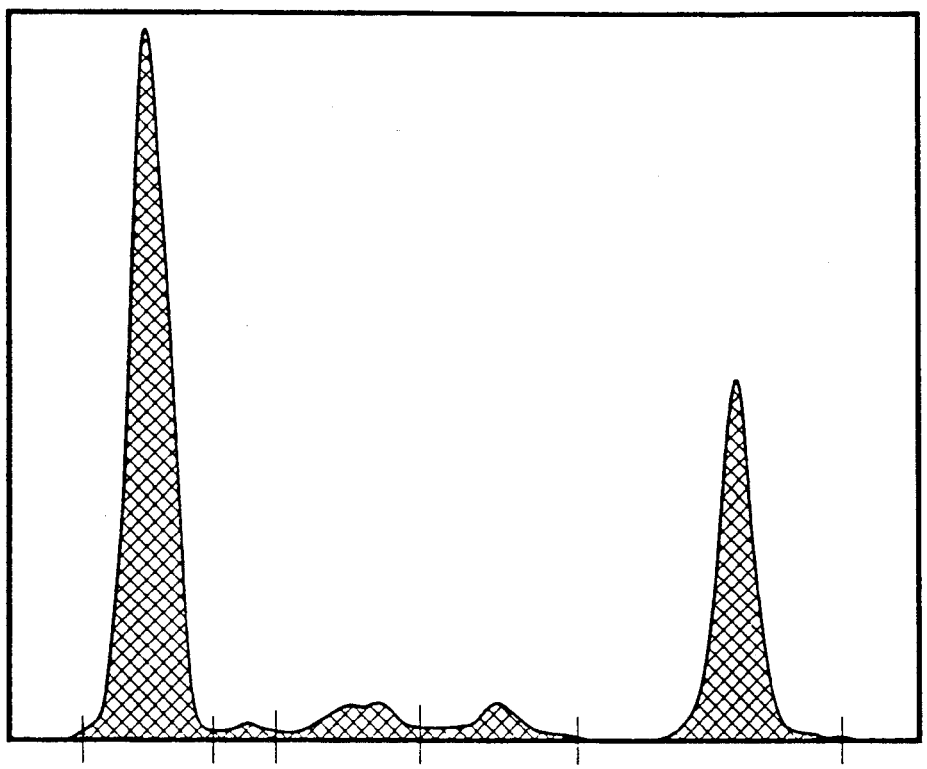
FIG. 3 is an electropherogram of an IgG kappa myeloma patient serum sample separated into its constituents by slab electrophoresis.

Analysis of a serum sample from an IgG kappa myeloma patient as analyzed using the same conditions described in Example 1, produced the electropherogram in FIG. 3.

Example 4

Serum Sample—IgG Kappa Myeloma CZE

Figure 4:
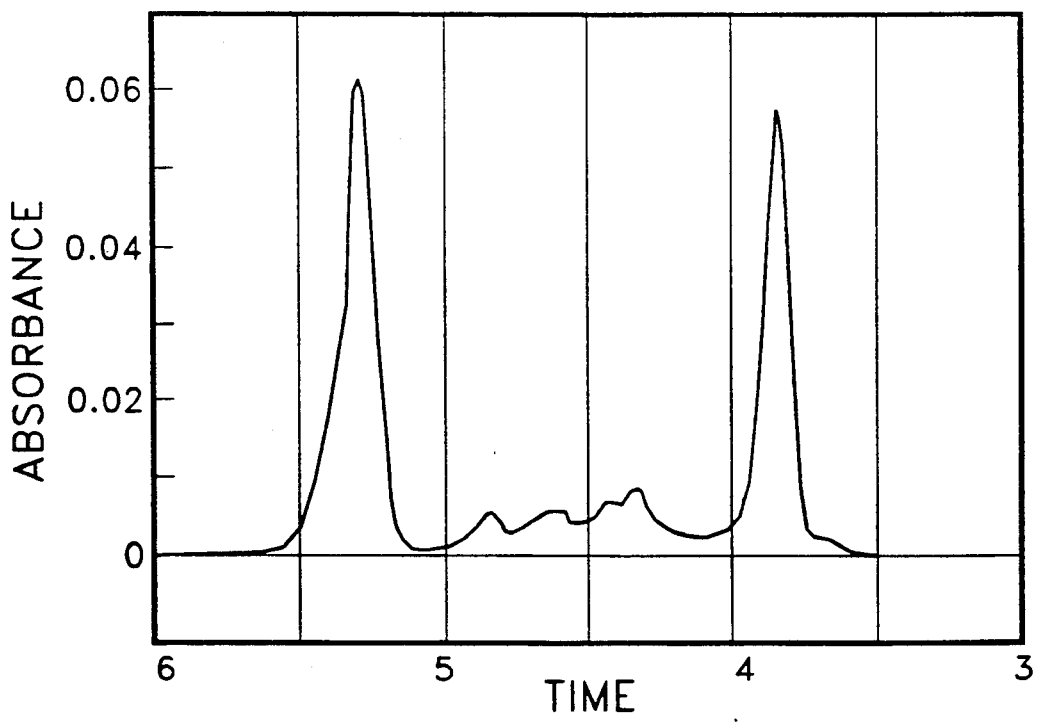
FIG. 4 is an electropherogram of the IgG kappa myeloma patient serum sample of FIG. 3 separated into its constituents by CZE.

Serum sample from the patient described in Example 3 was analyzed using the same conditions described in Example 2. The analysis produced the electropherogram in FIG. 4.

Example 5

Figure 5:
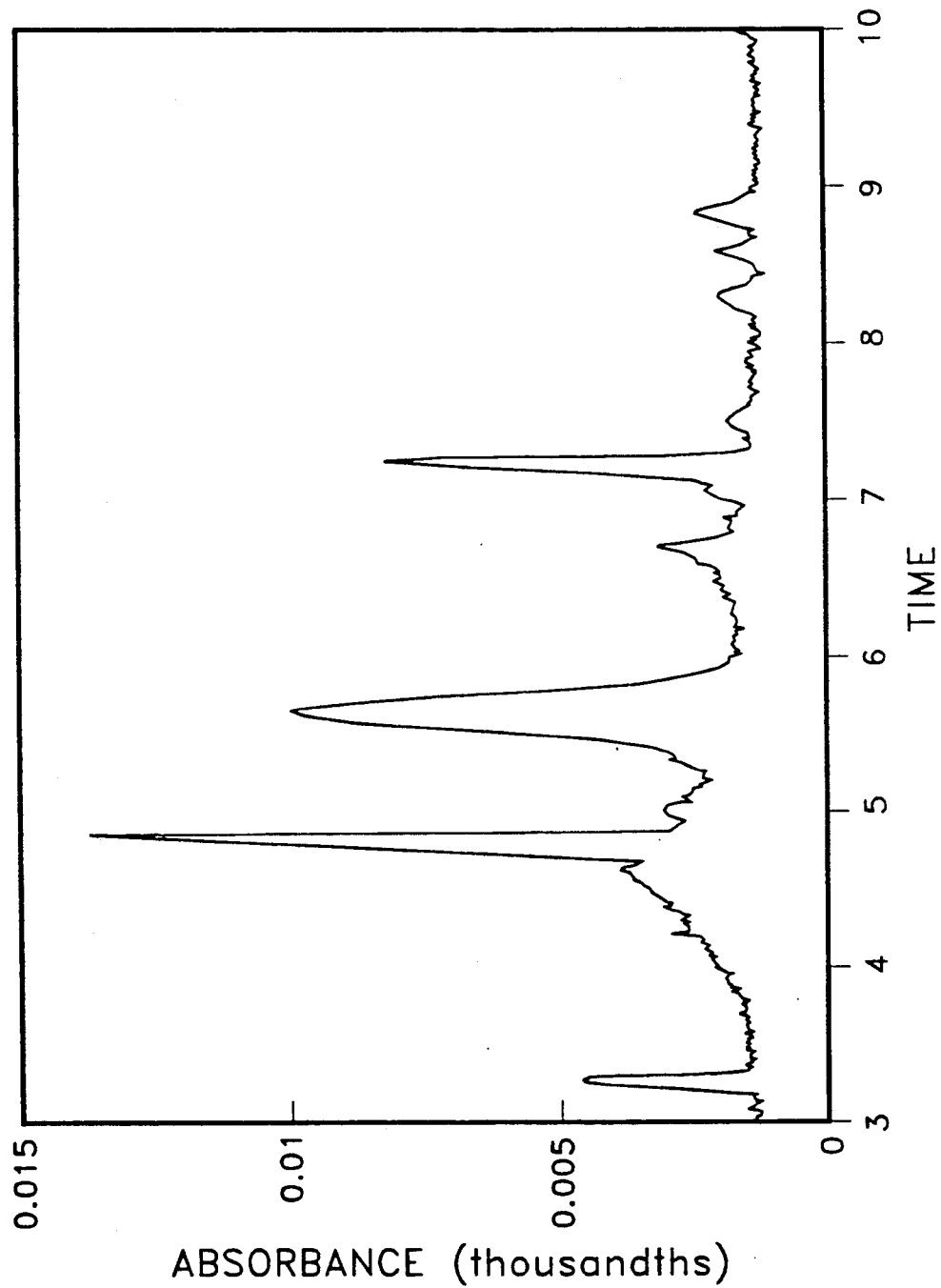
FIG. 5 is an electropherogram of a cerebrospinal fluid sample separated into its constituents by CZE.

Cerebro Spinal Fluid Sample CZE Patient cerebro spinal fluid sample was analyzed using the same conditions described in Example 2. The analysis produced the electropherogram in FIG. 5.

Example 6

Cerebro Spinal Fluid Sample CZE

Figure 6:
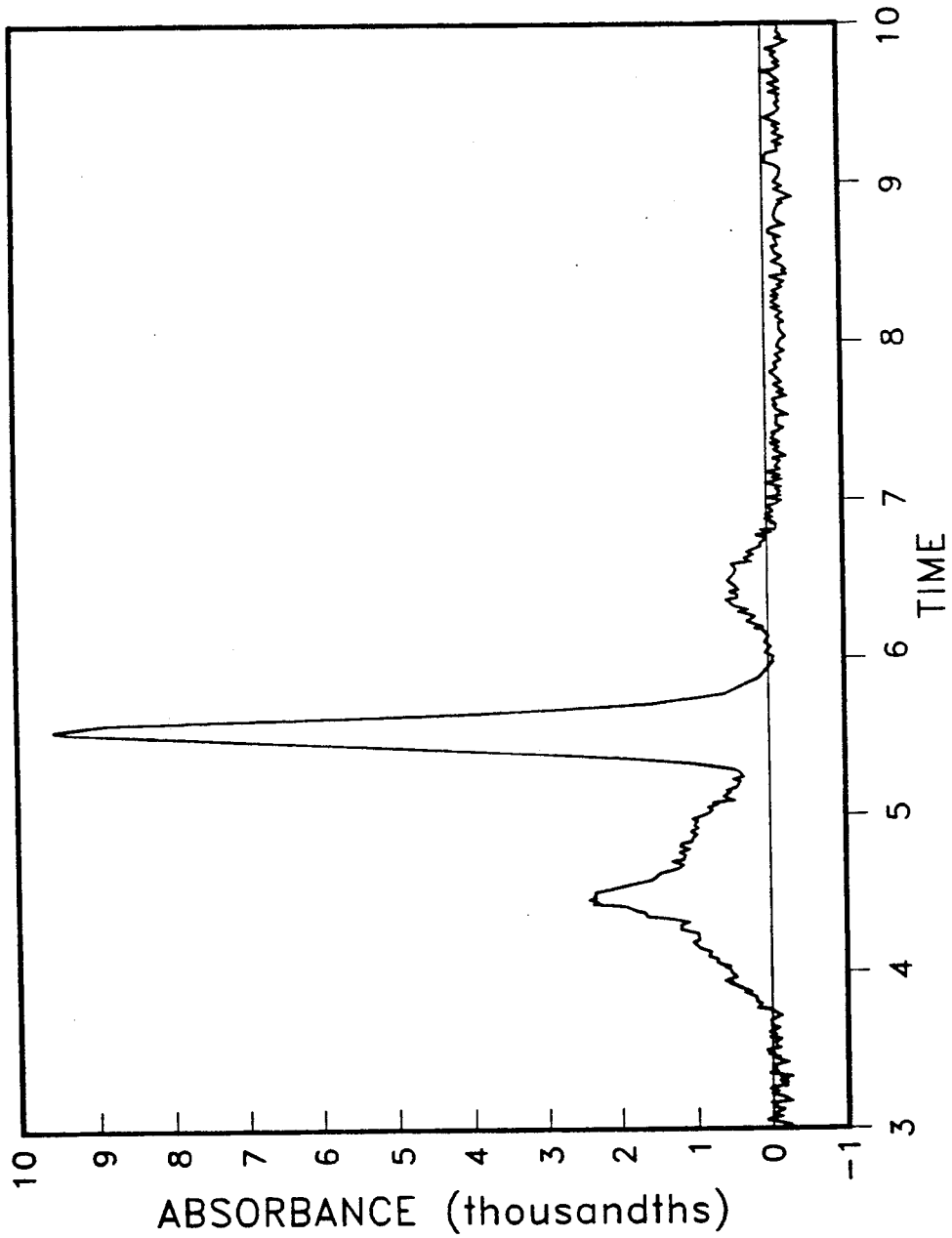
FIG. 6 is an electropherogram of the same cerebrospinal fluid sample of FIG. 5, dialyzed with a molecular weight cut-off of 14K daltons, separated into its constituents by CZE.

The same patient cerebro spinal fluid sample, dialyzed with a molecular weight cut-off of 14 daltons was analyzed using the same conditions described in Example 2. The analysis produced the electropherogram in FIG. 6.

Example 7

Normal Urine Sample CZE

Figure 7:
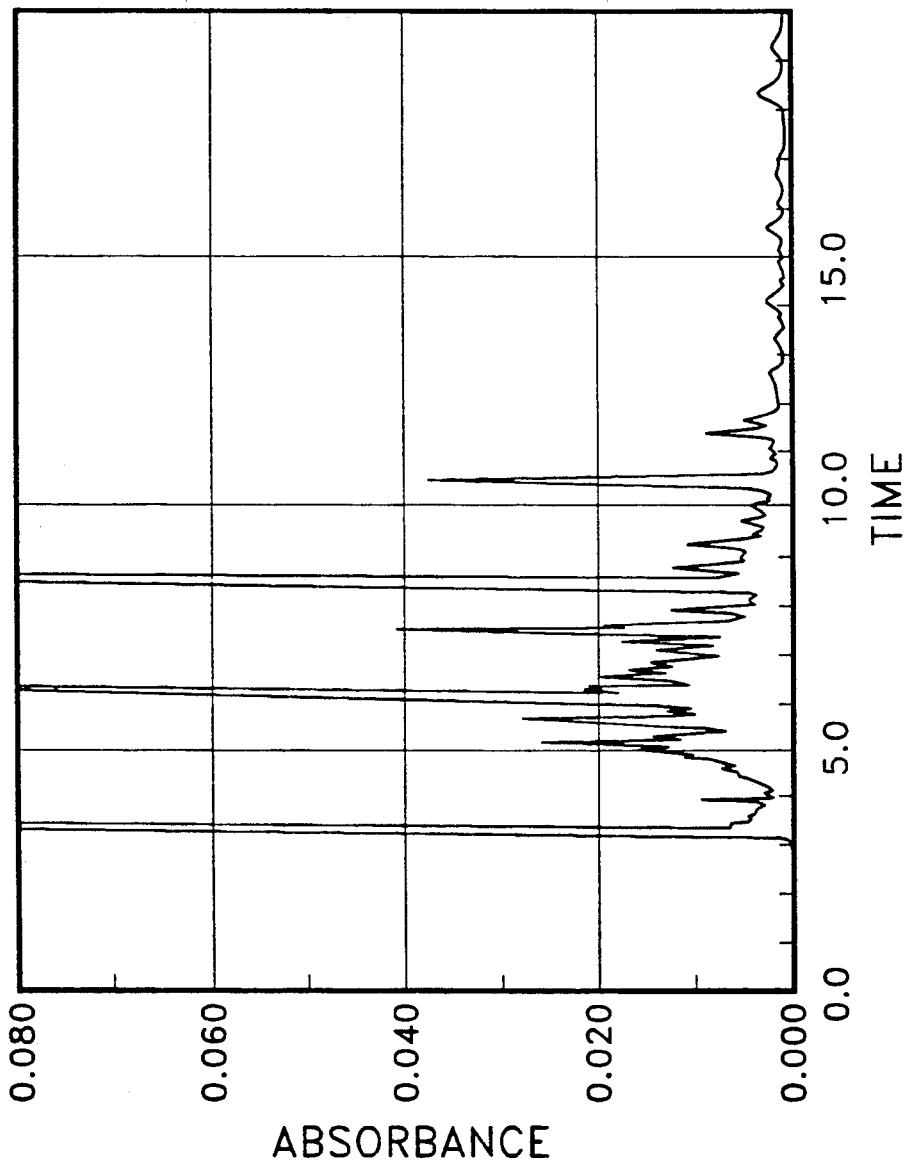
FIG. 7 is an electropherogram of a normal urine sample separated into its constituents by CZE.

Normal patient urine was analyzed as described in Example 2. The analysis produced the electropherogram in FIG. 7.

Example 8

Urine Sample—Bence Jones Proteins CZE

Figure 8:
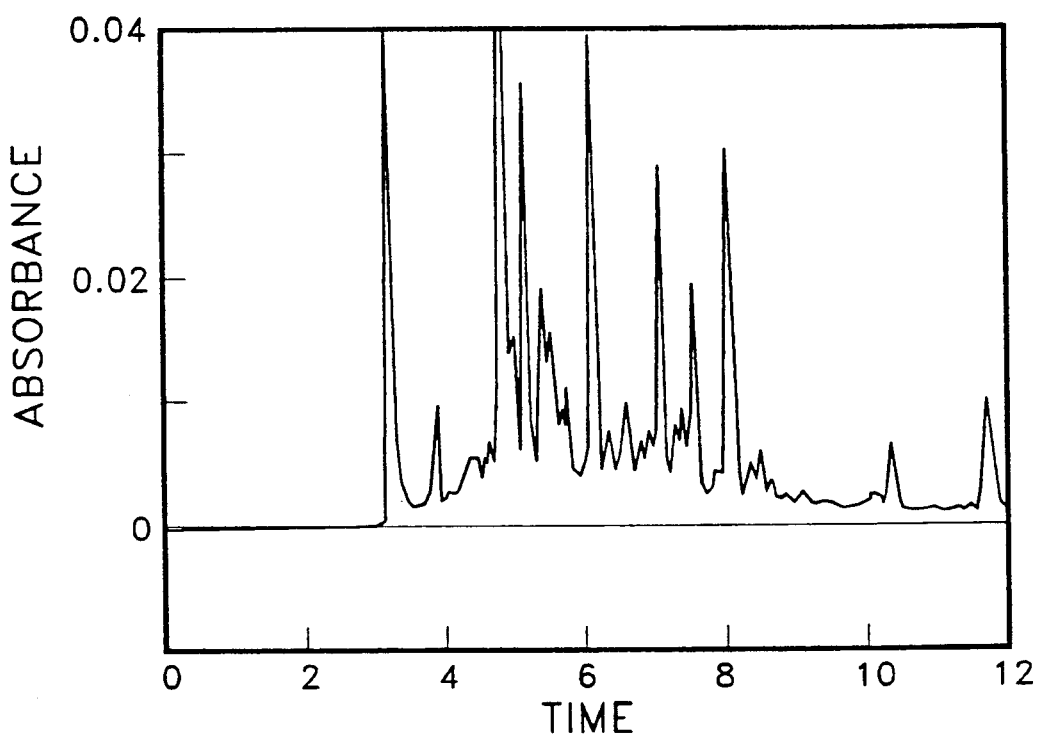
FIG. 8 is an electropherogram of a patient urine sample including Bence Jones proteins separated into its constituents by CZE.

Patient urine sample including Bence Jones proteins was analyzed using the conditions described in Example 7. The analysis produces the electropherogram in FIG. 8.

Example 9

CZE Reproducibility

Figure 9:
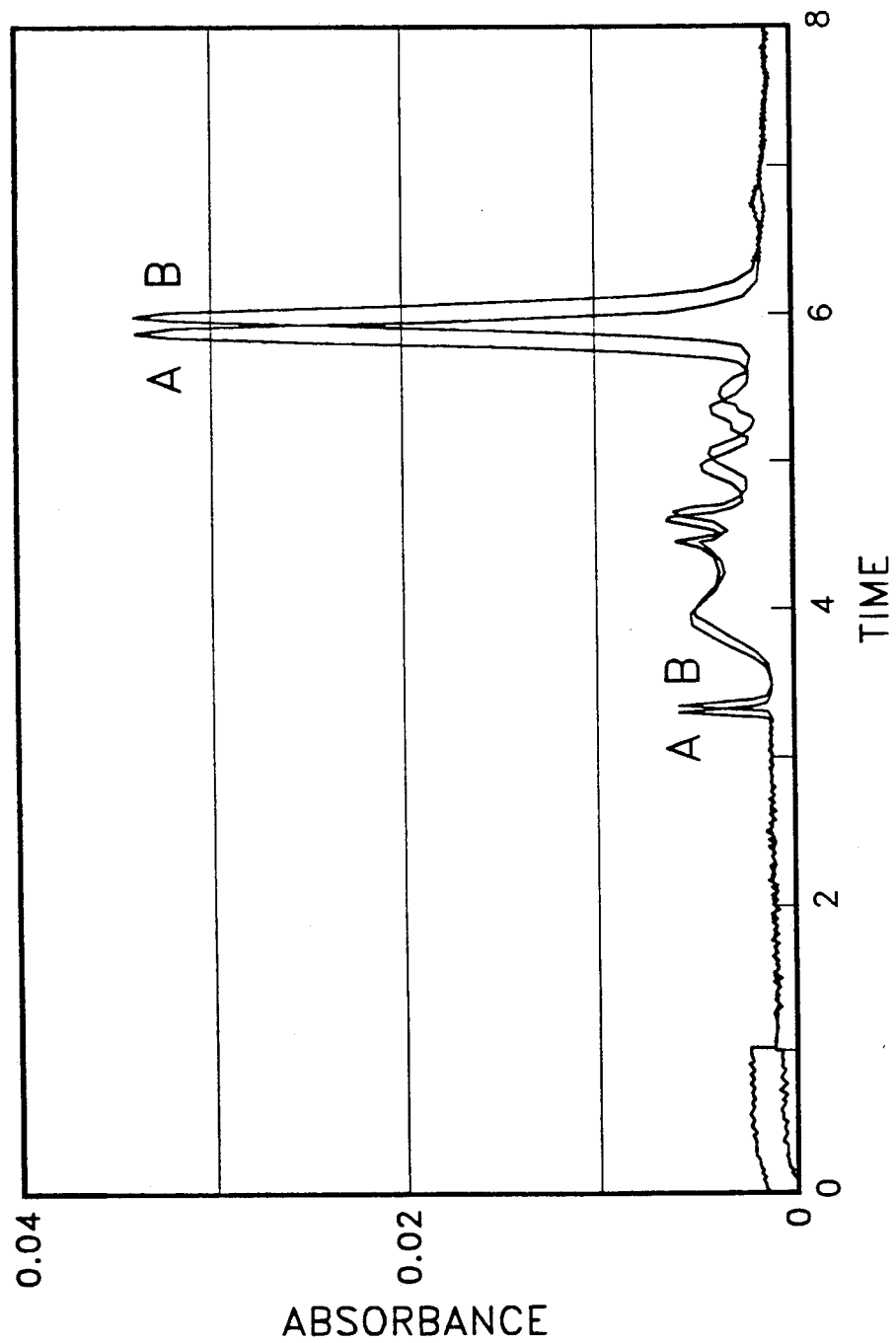
FIG. 9 is two superimposed electropherograms of normal serum proteins separated into their constituents by CZE, where electropherogram A is the 1st run and electropherogram B is the 20th run.

Using the conditions and sample described in Example 2, a reproducibility study of CZE analysis was conducted, with results being presented in FIG. 9. Electropherogram A is the 1st run of the sample and Electropherogram B is the 20th run of the sample.

The above data demonstrates that capillary zone electrophoresis of clinical samples in an untreated capillary column is possible utilizing the disclosed electrolyte buffer. Comparative testing of identical samples utilizing CZE and conventional slab electrophoresis indicates that the results produce nearly identical patterns. Furthermore, the data set forth in Example 9 indicates excellent reproducibility of the system, whereby after twenty repeated runs, the elution time of the peaks varies by less that 10 seconds. Accordingly, the foregoing data demonstrates the advantages and benefits which are derived from CZE analysis of clinical samples in untreated capillary columns.

While the foregoing electrolyte buffer and methodology has been described in considerable detail and in terms of preferred embodiments, they are not to be construed as limitations on the disclosure or the claims that follow. The invention is also not to be limited to the particular Beckman CZE analytical system described. Modifications and changes that are within the purview of these skilled in the art are intended to fall within the scope of the following claims.

What is claimed is:

1. A capillary zone electrophoresis method for the analysis of a clinical sample comprising glycoprotein constituents to be separated comprising the steps of:
   a) introducing into a capillary tube said clinical sample and an electrolyte buffer having a pH of about 10.0, said buffer comprising at least one agent capable of complexing with sugar moieties of glycoproteins, the concentration of said agent in said buffer being in stoichiometric excess relative to the glycoproteins of said sample,
   b) subjecting said sample to capillary zone electrophoresis techniques, and
   c) detecting the glycoprotein constituents of said sample.

2. The method of claim 1 wherein said complexing agent is selected from the group consisting of boric acid, alkylboronic acid having from about 1 to about 20 carbon atoms in the alkyl portion, lithium phosphate, sodium phosphate, potassium phosphate, rubidium phosphate, cessium phosphate, francium phosphate, mono-, di-, tri-, and tetra-alkyl ammonium phosphate having from about 1 to about 8 carbon atoms in the alkyl portion, lithium carbonate, sodium carbonate, potassium carbonate, rubidium carbonate, cessium carbonate, and francium carbonate, mono-, di-, tri, and tetra-alkyl ammonium carbonate having from about 1 to about 8 carbon atoms in the alkyl portion.

3. The method of claim 1 wherein the concentration of said complexing agent in said buffer is greater than about 20 mM.

4. The method of claim 1 wherein said complexing agent is boric acid.

5. The method of claim 4 wherein the concentration of said boric acid in said buffer is between about 70 mM and about 400 mM.

6. The method of claim 1 wherein said buffer further comprises an effective amount of at least one pH modifier.

7. The buffer of claim 6 wherein said pH modifier is selected from the group consisting of lithium hydroxide, sodium hydroxide, potassium hydroxide, rubidium hydroxide, cessium hydroxide and francium hydroxide, mono-, di-, tri-, and tetra-alkyl ammonium hydroxide having from between about 1 and about 8 carbon atoms in the alkyl portion.

8. The buffer of claim 6 wherein said pH modifier is sodium hydroxide.

9. The buffer of claim 1 wherein the pH of said buffer is between about 9.0 and about 12.0.

10. The method of claim 1 wherein said sample is selected from the group consisting of whole blood, serum, plasma, urine and cerebro spinal fluid.

11. A capillary zone electrophoresis method for the analysis of a clinical sample comprising glycoprotein constituents to be separated comprising the steps of:
   a) introducing into a capillary tube said clinical sample and an electrolyte buffer having a pH of at least about 10.0, said buffer comprising boric acid, the concentration of said boric acid being in stoichiometric excess relative to the glycoproteins of said sample;
   b) subjecting said sample to capillary zone electrophoresis techniques, and
   c) detecting the glycoprotein constituents of said sample.

* * * * *